(12) United States Patent
Jena et al.

(10) Patent No.: US 10,147,186 B2
(45) Date of Patent: Dec. 4, 2018

(54) MULTI-PARAMETER BASED TISSUE CLASSIFICATION

(71) Applicants: Amarnath Jena, New Delhi (IN); Sangeeta Taneja, New Delhi (IN); Shashi Bhushan Mehta, Greater Noida (IN)

(72) Inventors: Amarnath Jena, New Delhi (IN); Sangeeta Taneja, New Delhi (IN); Shashi Bhushan Mehta, Greater Noida (IN)

( * ) Notice: Subject to any disclaimer, the term of this patent is extended or adjusted under 35 U.S.C. 154(b) by 22 days.

(21) Appl. No.: 15/513,571

(22) PCT Filed: Sep. 7, 2015

(86) PCT No.: PCT/IB2015/056830
§ 371 (c)(1),
(2) Date: Mar. 23, 2017

(87) PCT Pub. No.: WO2016/051297
PCT Pub. Date: Apr. 7, 2016

(65) Prior Publication Data
US 2017/0301086 A1    Oct. 19, 2017

(30) Foreign Application Priority Data

Sep. 30, 2014   (IN) .......................... 2799/DEL/2014

(51) Int. Cl.
| | |
|---|---|
| G06K 9/00 | (2006.01) |
| G06T 7/00 | (2017.01) |
| A61B 5/055 | (2006.01) |
| A61B 6/03 | (2006.01) |
| A61B 5/00 | (2006.01) |
| A61B 6/00 | (2006.01) |

(52) U.S. Cl.
CPC .......... *G06T 7/0012* (2013.01); *A61B 5/0035* (2013.01); *A61B 5/055* (2013.01); *A61B 6/037* (2013.01); *A61B 6/481* (2013.01); *A61B 6/5217* (2013.01); *A61B 6/5247* (2013.01); *A61B 6/4417* (2013.01); *G06T 2207/10024* (2013.01); *G06T 2207/10081* (2013.01); *G06T 2207/10088* (2013.01); *G06T 2207/10104* (2013.01); *G06T 2207/30096* (2013.01)

(58) Field of Classification Search
CPC ................. G06T 7/0012; G06T 7/0083; G06T 2207/30004; G06T 7/0081; G06F 19/321
See application file for complete search history.

(56) References Cited

U.S. PATENT DOCUMENTS 8,842,896 B2 * 9/2014 Hajnal ................... A61B 5/055
                                                                            382/131

FOREIGN PATENT DOCUMENTS

WO    WO2006/054193    *    5/2006   ............... G06T 3/00

OTHER PUBLICATIONS

The Journal of Diagnostic and Interventional Neuroradiology, American Journal of Neuroradiology, Sep. 2013, vol. 34, No. 9.*

* cited by examiner

*Primary Examiner* — Duy M Dang
(74) *Attorney, Agent, or Firm* — Cesari & McKenna, LLP

(57) ABSTRACT

The present disclosure addresses above-mentioned issues by providing a system and method for preparing a correlation data set to be used in parametric grading of malignant tissues. Systems and methods of the present disclosure further provide for a visualization scheme, wherein all the parameters can be viewed at the same time and processed together to arrive at an accurate grading of the tissue based on threshold based comparison of the parameter values for each voxel.

9 Claims, 6 Drawing Sheets

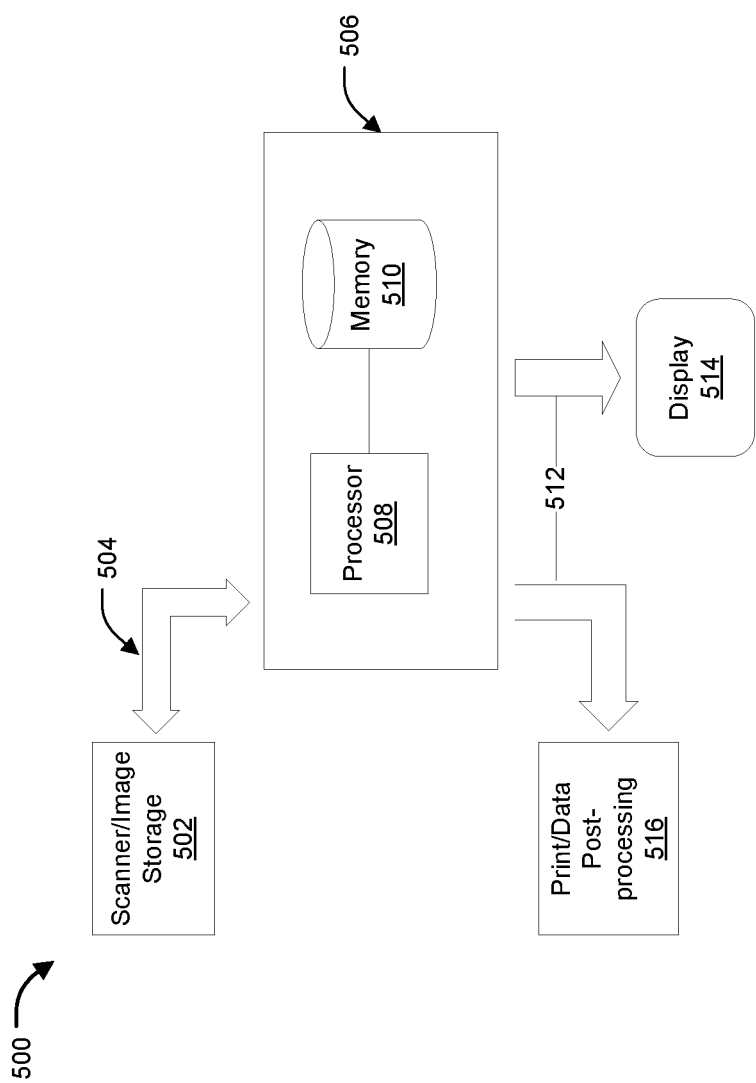

MULTI-PARAMETER BASED TISSUE CLASSIFICATION

CROSS REFERENCE TO RELATED APPLICATIONS

This application is the National Stage of International Application No. PCT/IB2015/056830, filed on Sep. 7, 2015, which claims the benefit of Indian Application No. 2799/DEL/2014, filed on Sep. 30, 2014. The contents of both applications are hereby incorporated by reference in their entirety.

FIELD OF THE INVENTION

The present disclosure relates to a system and method for detection of tumor through PET-MRI technology for accurate, reliable, and reproducible evaluation and classification of tissues. More specifically, the present disclosure relates to tumor characterization from PET and MR image data based on a combination of a plurality of MR image-based parameters and PET image based parameters.

BACKGROUND OF THE INVENTION

Background description includes information that may be useful in understanding the present invention. It is not an admission that any of the information provided herein is prior art or relevant to the presently claimed invention, or that any publication specifically or implicitly referenced is prior art.

Magnetic resonance imaging ("MRI") is a well-known, highly useful technique for diagnosing abnormalities in biological tissues. MRI can detect abnormalities that are difficult or impossible to detect by other techniques, without the use of x-rays or invasive procedures. Also, MRI is widely used technique for grading tumors, especially for malignant gliomas (brain tumors) due to their inherent inaccessibility.

However, till date, conventional MRI has not been capable enough to distinguish accurately between normal, benign, and malignant tissues. This is primarily because tissues have a number of distinguishing characteristics, which change for each patient and the tissue being monitored, and therefore a fixed threshold for classifying the tissue is not possible.

Magnetic Resonance Imaging (MRI) uses multiple quantitative and qualitative parameters and attributes that are evaluated and measured pre and post injection of the contrast for determining and classifying the tissue/lesion under investigation. Apparent diffusion coefficient (ADC) is one such quantitative parameter, which measures magnitude of diffusion (of water molecules) within tissue. A low ADC value indicates higher compactness of cells in a unit area and indicates towards malignancy, whereas high ADC, on the other hand, indicates less compactness of cells in a unit area and indicates towards benignity. The objective of using ADC as a parameter is to determine water diffusion in tissue region, wherein a lower value of ADC indicates decrease in inter cellular space as seen in cancerous tissues. Diffusion MRI is also used in evaluating effectiveness of treatment by monitoring water diffusion values for the tissue region. Diffusion MRI can be used to assess treatment effect through quantification of the amount of increased apparent diffusion coefficient (ADC) values in tumor regions experiencing a loss of cellular density. However, ADC is sensitive to changes in tissue microstructure and depends on a number of variable attributes such as "b values", which make the ADC estimate unreliable and noise sensitive.

Magnetic Resonance Spectroscopy (MRS) is also commonly used for non-invasive examination of metabolic characteristics of human cancers in a clinical environment. Accessible nuclei include 31P, 13C, 1H, and 23Na. 31P MRS contains information about energy status (phosphocreatine, inorganic phosphate, and nucleoside triphosphates), phospholipids metabolites (phosphomonoesters and phosphodiesters), intracellular pH (pH NMR), and free cellular magnesium concentration (Mg2+f). Water-suppressed 1H MRS, a frequently used technique, shows total choline, total creatine, NAA (N-Acetyl L-Aspartate), lipids, glutamate, inositols, lactate, and the like. Choline/Creatine, Choline/NAA (N-Acetyl Aspartate), Lipid and Lactate ratios are a commonly used parameters used as biomarker to classify tissues. Negendank, W., NMR in Biomedicine, 5, 303-324 (1992). (Harish 1995 AJNR ref—*AJNR Am J Neuroradiol* 16:1593-1603, September 1995.

Positron Emission Tomography ("PET") is an imaging technology that depicts distribution of radiotracers that get accumulated in a tissue (uptake) proportionate to metabolism and tissue function. The device can provide body tissue related molecular and functional information in very high contrast. PET tracers such as flurodeoxyglucose (FDG) and FluoroEthyleTyrosineare used to depict higher uptake in cancer tissue and lower uptake in benign lesions.

However, since a PET device fundamentally has a low resolution, there is a limitation in providing anatomical information. In contrast, an MRI device can provide detailed anatomical information about body tissues, but has a limitation in providing molecular and functional information when compared with a PET device.

Dynamic susceptibility perfusion imaging is a MRI technique, which is based on dynamic contrast enhancement (DCE) and is widely used for grading tumors, especially for gliomas. Perfusion imaging of tumors is becoming increasingly important due to its usefulness to demonstrate vascular growth (angiogenesis and neovascularization) associated with tumor growth by imaging the Blood Volume (BV) or Blood Flow (BF) in a tumor.

Blood volume map (BV)or Blood flow (BF) maps provide volume of blood in a region of tissue. The blood volume can be used to evaluate micro-vascular density or vascularity, in other words, density of small blood vessels (capillaries) in a tissue region. Perfusion imaging whereby images are acquired before, during and after injection of a contrast agent and BV values are calculated to correlate with the grade of vascularity; high-grade (malign) tumors tend to have higher BV values than low-grade (less malign) tumors. In practice high and low grade gliomas based on relative cerebral blood volume (rCBV) maps are obtained by perfusion MRI. A general way to characterize glioma malignancy is by measuring the ratio between the most elevated rCBV area within the glioma ("hot-spot"), and an unaffected contra-lateral white matter rCBV value. Although several notations are used, this ratio is often referred to as normalized CBV (nCBV), and high-grade gliomas tend to have a higher nCBV ratio than low-grade gliomas. Perfusion imaging is therefore helpful in the grading of tumors. However, due to relatively small voxel sizes (typically tens of mm2) of the perfusion imaging technique, large vessels in the region could result in a misleading shift of the BV frequency distribution towards higher BV values. Hence, it is necessary to develop an improved method to quantify and validate errors involved in calculating the voxel size from dynamic perfusion imaging technique, improve accuracy of correct classification/categorization/characterization of malignant and non-malignant tissues.

With the advent of simultaneous PET-MRI, it is possible to obtain voxel wise multiparametric information from all the MR based parameters like ADC from Diffusion images, nCBV or/and nCBF from perfusion images, Choline/Creatine from proton MR Spectroscopy and SUV from PET in a single examination. The present disclosure envisages to develop a time efficient, reliable and reproducible diagnostic technique and tool for voxel wise analysis of clustered parameters on individual weighing towards tissue characterization derived from MRI and PET for characterization of tissues based on parametric mapping.

The present invention satisfies these needs, as well as others, and efficiently overcomes the deficiencies found in the background art.

OBJECTS OF THE INVENTION

It is an object of the present disclosure to detect and diagnose post treatment changes in malignant tissues through PET-MRI technology.

It is an object of the present disclosure to classify tissues as being malignant based on a combination of outputs from multiple MRI and PET image-based parameters.

It is an object of the disclosure to design and develop a time efficient, reliable and reproducible diagnostic technique for accurate analysis of malignant tissues and non-malignant tissues based on parametric mapping so as to distinguish malignant from non-malignant tumors.

It is an object of the present disclosure to provide a new and more precise approach to classify tissues through PET-MRI technology.

It is another object of the present disclosure to use parametric mapping for identification of the most malignant tissue to help clinician's before surgery, treatment, radiotherapy, sterotactic biopsy and response therapy.

It is yet another object of the present disclosure to develop a cost effective PET-MRI technique (time efficient imaging and evaluation) against standard MRI and PET technique, with an aim to bring PET-MRI for wider use and as a possible preferred standard technique.

SUMMARY OF THE INVENTION

The present disclosure addresses above-mentioned issues by providing a system and method for preparing a correlation data set to be used in parametric grading of malignant tissues. Systems and methods of the present disclosure further provide for a visualization scheme, wherein all the parameters can be viewed at the same time and processed together to arrive at an accurate grading of the tissue based on threshold based comparison of the parameter values for each voxel. In an aspect of the present disclosure, system and method of the present disclosure use a combination of three MR parameters, namely relative cerebral blood volume (rCBV), Choline/Creatine ratio (Cho/Cr), apparent diffusion coefficient (ADC), and one PET parameter, namely maximum standardized uptake value (SUV Max) parameter to accurately evaluate whether a tissue is malignant or not.

In an aspect, system of the present disclosure provides for acquisition of MR image and PET image of a tissue by means of a (multiple modality medical system or on an individual basis PET and MRI system) MR-PET device, and superimposition of a voxel grid on the acquired image(s). System can also provide for computation of above-mentioned parameters, namely rCBV, Cho/Cr, ADC, and SUV Max for each voxel so as to arrive at four parameter values for each voxel, and comparison of each parameter value for each voxel with a threshold value that corresponds to the parameter in context in order to determine whether, for that parameter or as per that parameter, the concerned area mapped to the voxel is malignant. Similarly, for each voxel, comparison for all the four parameter values can be performed with their respective threshold values to determine number of parameters and/or details/attributes thereof that indicate the tissue part corresponding to the voxel to be malignant.

In another aspect, based on the number of parameters (of the four parameters) that evaluate the respective tissue part to be malignant, a color can be associated with the corresponding voxel grid to indicate probability of the corresponding tissue part to be malignant. For instance, red color can be associated with a voxel in case all the parameter values for that voxel are above their respective thresholds, brown color can be associated with a voxel in case three parameter values for that voxel are above their respective thresholds, green color can be associated with a voxel in case two parameter values for that voxel are above their respective thresholds, and yellow color can be associated with a voxel in case only one out of the parameter values for a voxel is above its respective threshold. Similarly, the voxel grid can be colored for each voxel.

In another aspect of the present disclosure, weights can also be associated with each parameter, wherein the weights can indicate relative importance of the respective parameter in evaluation of a tissue being malignant. For instance, in an embodiment, weights of all the four parameters rCBV, Cho/Cr, ADC, and SUV Maxcan be equal (i.e. 0.25 each), and in another embodiment, parameter ADC can have a high relative weight of say 0.4 when compared with the weight of Cho/Cr, which can be 0.15.

In an aspect of the present disclosure, the proposed method can include administrating one or more MR based biomarkers or PET tracers for enabling generation of PET-MR image, wherein the generated image can then be acquired and a voxel grid can be superimposed over the acquired image. Method of the present disclosure can further include obtaining one or more metabolite signals from the acquired image data and computing various PET-MRI parameters, including rCBV, Cho/Cr, ADC, and SUV Max, wherein rCBV, Cho/Cr, and ADC parameters can be computed from the MR-image and SUV Max parameter can be computed from PET-image, wherein both, the MRI image data and the PET image data can be from the same spatial location. In an implementation, using the acquired MRI image data as anatomical base and superimposing on the anatomical base image, a voxel grid can be obtained from spectroscopy data or other means.

In an aspect, PET-MRI technique of the present disclosure can include contrast agents/tracers for assessment of PET/MRI parameters. The contrast agents/tracers can include, but are not limited to Gadolinium (Gd), GadopentatedimeglumineGd-DTPA, FDG and other FDA approved Gd based contrast agents such as Omniscan, Multihance, Magnevist, Prohance, OptiMARK, Dotarem or other PET tracers including but not limited to FDG but other FDA approved products like FET, FLT, FMISO, Methionine.

It has been found therefore that a combination of rCBV, Cho/Cr, ADC, and SUV parameters for evaluation of their values and comparison of such values with respective parameter thresholds significantly enhances the accurate/reliable characterization of a tissue for malignancy detection, along with contributing to delineation of malignant region vizglioblastomasin brain, offering information not available with conventional MRInor PET individually. This approach may enhance the assessment of brain gliomas (malignant region), distinguishing areas of disease recurrence from treatment effect like radiation induced necrosis, providing useful information for guiding stereotactic biopsies, easier detections, surgical resection and radiation treatment.

In another aspect, although the present disclosure has been explained with respect with to one threshold value for each parameter, one should appreciate that multiple threshold values can be configured for each parameter such as for ADC and/or SUV, wherein each such threshold value can help classify the underlying tissue part as being malignant, or normal or benign or help present/evaluate any other attribute of the tissue part. Classification of each tissue part based on a combination of the above-mentioned four parameters with respect to one or more parameter-threshold values can help characterize the tissue part more comprehensively and accurately with multiple attributes.

In another aspect, although the color coding for each voxel has been described with respect to four colors (depending on the number parameters that have their values above a defined threshold), any number of colors can be configured for a combination of the four parameters depending on the number of threshold values, mode of comparison, weight of each parameter, way in which the parameter values have been combined for visual presentation. Therefore, one should appreciate that all such color combinations, mode of combination of parameters, and association of color-coding to voxels of a grid are completely within the scope of the present disclosure.

In yet another aspect, although the present application finds particular application in combined PET-MR medical imaging systems, it would be appreciated that the described technique may also find application in other diagnostic systems other imaging scenarios, or other diagnostic techniques (on an individual modality bases or multiple modality system).

Various objects, features, aspects and advantages of the inventive subject matter will become more apparent from the following detailed description of preferred embodiments, along with the accompanying drawing figures in which like numerals represent like components.

BRIEF DESCRIPTION OF DRAWINGS

FIG. 3(*b*) illustrates a colored representation 350 of the voxel grid in accordance with an embodiment of the present disclosure.

FIG. 5 illustrates an exemplary computer system diagram used for generating and analyzing a colored voxel grid to determine whether a tissue or part thereof is malignant in accordance with an embodiment of the present disclosure.

DETAILED DESCRIPTION OF THE INVENTION

Figure 1:
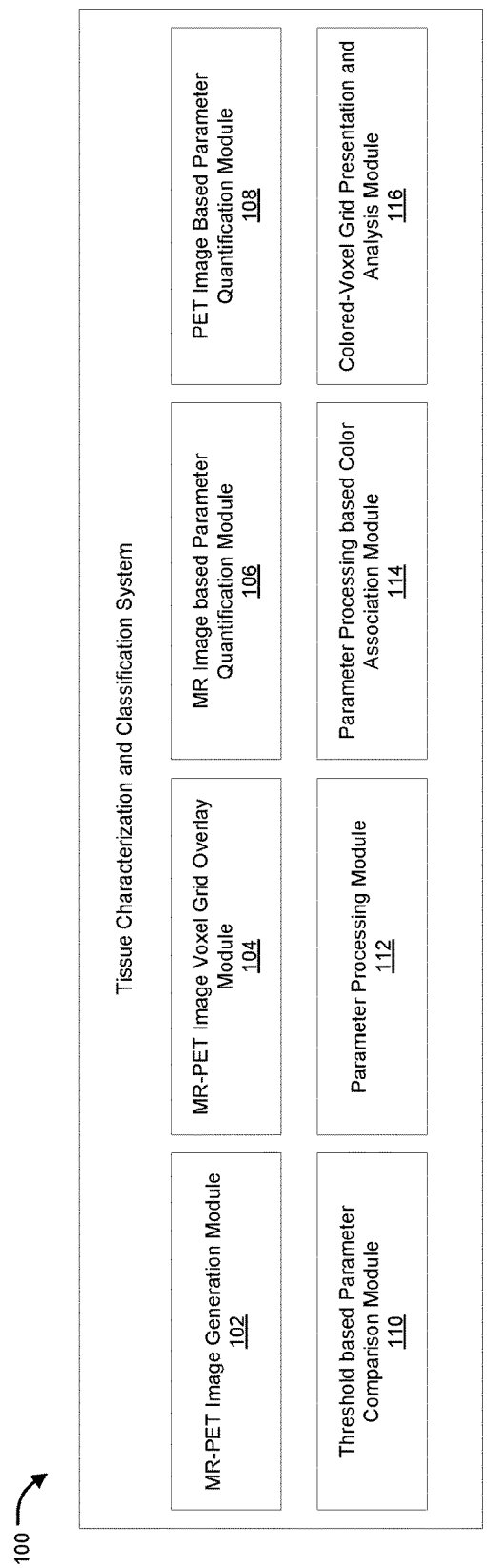
FIG. 1 illustrates exemplary functional modules of the proposed tissue characterization and classification system in accordance with an embodiment of the present disclosure.

Unless the context requires otherwise, throughout the specification and claims which follow, the word "comprise" and variations thereof, such as, "comprises" and "comprising" are to be construed in an open, inclusive sense that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and abstract of the disclosure provided herein are for convenience only and do not interpret the scope or meaning of the embodiments.

Reference will now be made in detail to the exemplary embodiments of the present disclosure, examples of which are illustrated in the accompanying drawings. Wherever possible, the same reference numbers are used in the drawings and the description to refer to the same or like parts.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

The present disclosure addresses above-mentioned issues by providing a system and method for preparing a correlation data set to be used in parametric grading of malignant tissues. System and method of the present disclosure further provide for a visualization scheme, wherein all the parameters can be viewed at the same time and processed together to arrive at an accurate grading of the tissue based on threshold based comparison of the parameter values for each voxel. In an aspect of the present disclosure, system and method of the present disclosure use a combination of three MR parameters, namely relative cerebral blood volume (rCBV), Choline/Creatine (Cho/Cr), apparent diffusion coefficient (ADC), and one PET parameter, namely standardized uptake value (SUV) parameters to accurately evaluate whether a tissue is malignant or not.

In an aspect, system of the present disclosure provides for acquisition of MR image and PET image of a tissue, and superimposition of a voxel grid on the acquired image(s). System can also provide for computation of above-mentioned parameters, namely rCBV, Cho/Cr, ADC, and SUV for each voxel, and comparison of each parameter value for each voxel with a threshold value to determine whether, for that parameter or as per that parameter, the concerned area mapped to the voxel is malignant. Similarly, for each voxel, comparison for all the four parameter values can be performed with their respective threshold values, to determine the parameters that indicate the tissue part corresponding to the voxel to be malignant.

In another aspect, based on the number of parameters (of the four parameters) that evaluate the respective tissue part to be malignant (by having their values greater than defined respective thresholds), a color can be associated with the corresponding voxel grid to indicate probability of the corresponding tissue part to be malignant. For instance, red color can be associated with a voxel in case all the parameter values for that voxel are above their respective thresholds, brown color can be associated with a voxel in case any three parameter values for that voxel are above their respective thresholds, green color can be associated with a voxel in case any two parameter values for that voxel are above their respective thresholds, and yellow color can be associated with a voxel in case anyone of the parameter values for that voxel are above their respective thresholds. Similarly, the voxel grid can be colored for each voxel.

FIG. 1 illustrates exemplary functional modules 100 of the proposed tissue characterization and classification system (also interchangeably referred to as 100 hereinafter) in accordance with an embodiment of the present disclosure. As shown, the system 100 can include a MR-PET image generation module 102 configured to inject a contrast agent/tracer into the body of the patient for improving visibility of internal body structures, and then generating an MR image and a PET image using a suitable MR-PET machine/scanner to retrieve functional information along with anatomy and tissue characterization such as information on soft tissue anatomy and blood vessel physiology. MR image and PET image can then be fused to combine anatomic and multi-parametric imaging of MRI with molecular information of PET. In an embodiment, MR image can be segmented and used to identify different tissues types, such as soft tissue, cortical bone, air pockets, etc. In another embodiment, in order for carrying out a combined MR-PET examination, two tracers can be administered to a patient, of which one specifically accumulates in bone lesions, for example FDG and NaF. In accordance with at least one embodiment of the inventive method image dataset is created separated into a dataset of a least one of the tracers, based on anatomical assignments, and a projection image of the bone structure as an overview image of the skeletal system. Through this a separate FDG-PET examination and skeletal scintigraphy is replaced by a single examination with the same significance.

In an exemplary embodiment, system 100 can further include a MR-PET image voxel grid overlay module 104 configured to superimpose a voxel grid on an anatomical base image, wherein said base image can be considered as the final image resulting from fusion of the MR image and PET image and/or can be only the MR-image. The voxel grid can include a plurality of cells/voxels, each overlaying/superimposing on a particular tissue part. In an exemplary embodiment, the voxel grid can be a 7*7 grid having a total of 49 cells, wherein each voxel can be assigned a defined color to indicate the chances of the underlying tissue part being malignant based on parameter values of the four parameters selected for the purpose of the present disclosure.

In another exemplary embodiment, system 100 can further include an MR image based parameter quantification module 106 configured to, for each voxel, identify parameter values for rCBV (perfusion), Cho/Cr (spectroscopy), and ADC (diffusion) of the underlying tissue part, wherein relative cerebral blood volume (rCBV) can be obtained from dynamic contrast enhanced (DCE) maps. Dynamic susceptibility perfusion imaging technique can be used in PET-MRI scans, which, based on dynamic contrast enhanced (DCE), can be used for grading tumors, especially for tumors due to their inherent inaccessibility. The term 'perfusion' comprises several tissue hemodynamic parameters (cerebral blood volume—CBV, cerebral blood flow—CBF, and mean transit time—MTT) that can be derived from the acquired data. In the evaluation of tumors, however, CBV appears to be the most useful parameter. In an aspect, in MRI perfusion imaging, the intravascular paramagnetic contrast molecules cause a shortening of T2* relaxation, which results in signal loss. Relevant image types include dynamic contrast enhanced (DCE) images, T2-weighted images, T1-weighted images and diffusion weighted (DW) images. DCE images, as mentioned above, can be used to generate regional cerebral blood volume (rCBV) maps based on the analysis of the dynamic signal response following bolus injection of the contrast agent. High and low grade gliomas based on relative cerebral blood volume (rCBV) maps can be obtained by perfusion MRI. rCBV mirrors the neovascularization associated with tumor angiogenesis; in adults with glial tumors, angiogenesis is highly correlated to tumor grade, and the rCBV of most high-grade glial tumors is greater than that of low grade tumors. Perfusion MR imaging is increasingly being used as a diagnostic and research tool that provides maps of the regional variations in cerebral microvasculature of normal and diseased brains. rCBV and rCBF derived with other MRI technique Arterial Spin Labeling (ASL) achieved similar to T2* DCE MRI but not infusing any contrast media can be included in the embodiment as a parameter in its lieu.

Cho/Cr, on the other hand, can be obtained from spectroscopy images and higher Choline/Creatine ratio values indicate higher malignancy. Apparent diffusion coefficient (ADC) map values can be derived from DW images from MRI and can be configured to indicate rate of water diffusion at the respective tissue part. According to an embodiment, such parameter values can be computed from the MR-image for all the voxel cells so as to cover the entire issue in context. In an aspect of the present disclosure, diffusion weighted (DW) imaging, which is capable of measuring the random thermal (Brownian) motion of water, samples the tumor microenvironment on a sub cellular level, wherein a drop in tumor cellularity as a result of significant cell-kill following effective therapy has been associated with an increase in water diffusivity as expressed as the apparent diffusion coefficient (ADC) maps. ADC maps can be generated by analysis of the signal change as a function of diffusion weighting obtained from the DW images. DW imaging can be used as a surrogate imaging biomarker for treatment response assessment in oncology.

In another aspect, system 100 of the present disclosure can include a threshold based parameter comparison module 110 configured to compare, for every voxel, value of each of the four parameters with their corresponding pre-defined threshold value for that parameter in order to determine whether the parameter value is above the respective threshold value. Such a comparison can be done for all the four parameters with respective threshold values, and the process can be performed for each voxel of the grid to assess which parameters for a given voxel has its value greater than the respective threshold value. In an exemplary embodiment, threshold value for a given parameter can be consistent for all the voxels to ensure consistency in output, and threshold values can be defined such that in case a parameter value is greater than the respective threshold value, the underlying tissue part can be categorized as malignant from the point of view of that parameter. In another embodiment, threshold values can be different for different parameters with respect to the voxel being represented. In another embodiment, threshold values can also be configured and/or customized and/or modified as desired.

In another aspect, system 100 of the present disclosure can include a parameter processing module 112 configured to process outcomes of comparison conducted in module 110. In an exemplary implementation, determination can be made for each voxel in terms of the number of parameters (including details thereof) that have their values greater than respective thresholds. Actual parameter values can also be recorded and/or stored, in say a database. In an implementation, each parameter value of every voxel can be recorded with or without respective threshold values and can be represented in any desired format.

In an aspect, system 100 of the present disclosure can include a parameter processing based color association module 114 configured to associate a defined color to each voxel based on the number of parameters that have their values greater than respective threshold values for that voxel. In an instance, in case all the four parameters rCBV, Cho/Cr, ADC, and SUV have their values greater than respective threshold values for a given voxel, the voxel can be colored as red showing that the tissue part underlying the voxel is confirmed as being malignant by all the four parameters. Similarly, in case any of the three parameters have their values greater than respective threshold values for a given voxel, the voxel can be colored as brown showing that the tissue part underlying the voxel is confirmed as being malignant by three of the four parameters and one parameter believes the tissue part not being malignant. Similarly, in case any of the two parameters have their values greater than respective threshold values for a given voxel, the voxel can be colored as green showing that the tissue part underlying the voxel is confirmed as being malignant by two of the four parameters and two parameters believe the tissue part not being malignant. On the same lines, in case any one parameter has its values greater than respective threshold values for a given voxel, the voxel can be colored as yellow showing that the tissue part underlying the voxel is confirmed as being malignant by only one of the four parameters, and three parameters believe the tissue part not being malignant. In an embodiment, any other color as configured can be implemented and such changes are completely within the scope of the present disclosure. In another embodiment, each parameter can have same or different weights of importance. For instance, each of rCBV, Cho/Cr, ADC, and SUV can have a weight of 0.25 meaning that all four carry the same weight/importance. In another instance, rCBV and Cho/Cr can have weights of 0.3 each, and ADC and SUV can have a weight of 0.2 each. Any other such weight can be associated with the parameters and all such configurations are completely within the scope of the present disclosure. Therefore, for a decision making, colors can also be associated to voxels based on the weights that they carry. For instance, taking the above example, even in case ADC and SUV have values lower than respective threshold values (indicating non-malignant tissue) and rCBV and Cho/Cr have values higher than respective threshold values (indicating malignant tissue), because rCBV and Cho/Cr in the above example have a higher collective weight of 0.6, the color of the voxel can be made brown instead of green. One should appreciate that the above is only an exemplary embodiment, and any other combination, weight association, color association, or basis of color association is completely within the scope of the present invention.

In an aspect, system 100 of the present disclosure can include a colored-voxel grid presentation and analysis module 116 configured to enable a user to analyze the color of each voxel and determine whether the underlying tissue part is malignant. Analysis can also be made of the tissue as a whole. Furthermore, analysis can be also including the actual parameters that had values higher than respective thresholds and the reason of color association as presented. In an implementation, analysis of the colored voxel grid can enable a user/doctor to evaluate whether the tissue as whole or a part thereof is malignant.

One should appreciate that the number of modules can always be reduced/increased and they are logical in nature. Therefore any number of modules and/or sub-modules are within the scope of the present disclosure and their functionality can therefore be implemented in any other construction/structure/configuration in the form of say an engine/sub-system.

Figure 2:
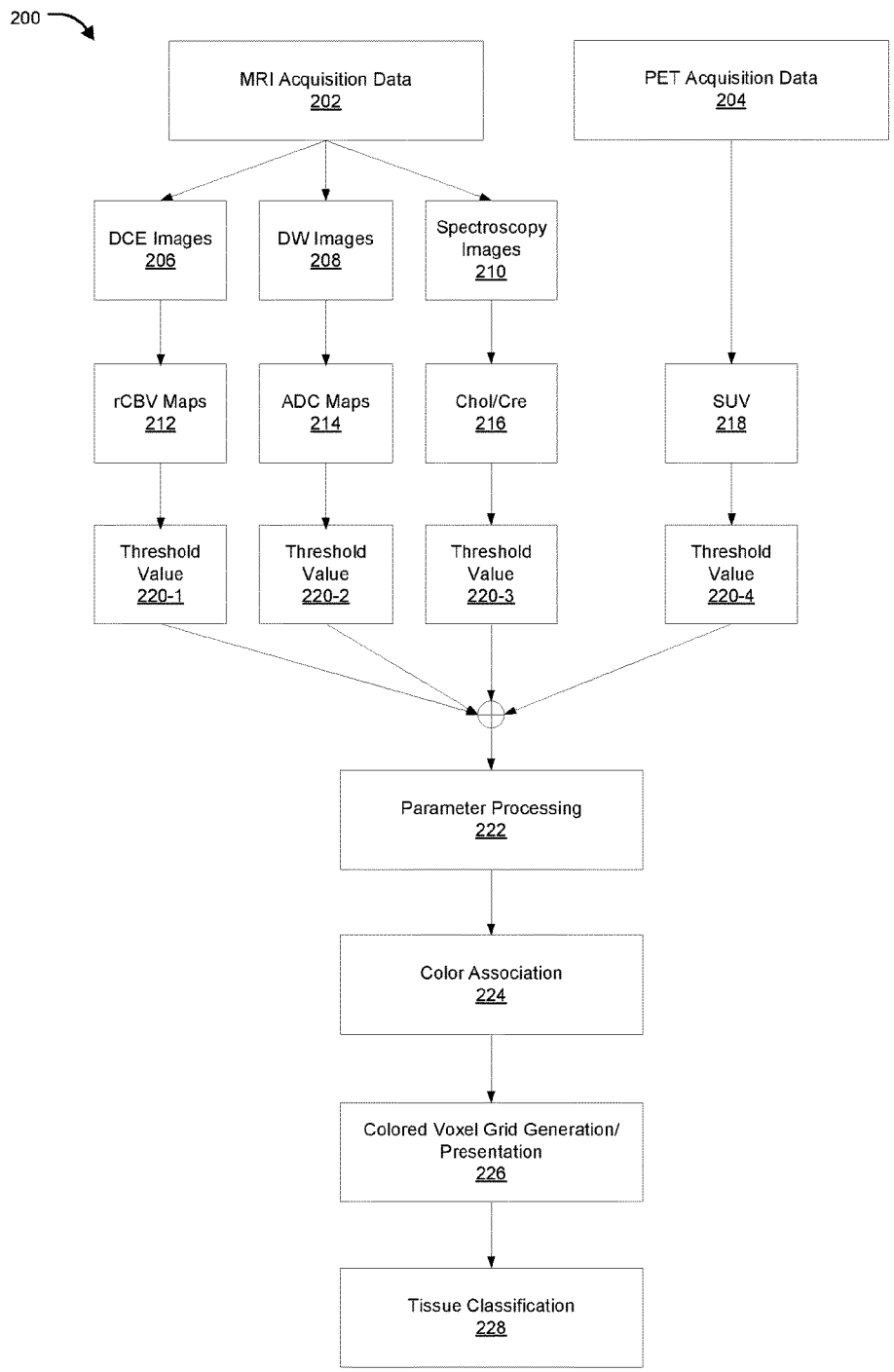
FIG. 2 illustrates an exemplary block diagram illustrating generation and analysis of a colored voxel grid to assess malignancy of a tissue or part thereof in accordance with an embodiment of the present disclosure.

FIG. 2 illustrates an exemplary block diagram 200 illustrating generation and analysis of a colored voxel grid to assess malignancy of a tissue or part thereof in accordance with an embodiment of the present disclosure. As illustrated, at block 202, data and/or parameter information can be obtained from an MR-image generated by means of say a MRI-PET machine. Such information/data can, in an exemplary embodiment, include one or a combination of DCE image(s) 206, DW image(s) 208, and spectroscopy image(s) 210. In an embodiment, DCE image(s) 206 can be processed to obtain rCBV maps 212, which can be used to obtain rCBV parameter value for each tissue part that corresponds to a voxel of a superimposed voxel grid. Similarly, in another embodiment, DW image(s) 208 can be processed to obtain ADC maps 214, which can be used to obtain ADC parameter value for each tissue part that corresponds to a voxel of a superimposed voxel grid. Therefore, a plurality of parameter values can be obtained for a tissue of which the MRI-PET image has been obtained, wherein the number of parameter values can be equal to the number of voxels that overlay/superimpose on the subject tissue by means of the voxel grid. Similarly, spectroscopy image(s) 210 can be processed to obtain a plurality of Cho/Cr parameter values 216 depending on the number of voxels that form part of a superimposed voxel grid that is overlaid on the tissue in context.

In an embodiment of the present disclosure, each parameter value 212/214/216 can be compared with a corresponding threshold value 220-1/220-3/220-3, collectively referred to as threshold value 220 hereinafter. Therefore, each parameter value of a given voxel can be compared with its respective threshold value 220 to determine whether the parameter value is greater than (or equal to) the threshold value 220. For instance, each rCBV parameter value 212 can be compared with its corresponding threshold value 220-1 (say 2.2) to determine whether its value is greater than the value 220-1. Similarly, each Cho/Cr parameter value 216 can be compared with its corresponding threshold value 220-3 (say 1.8) to determine whether its value is greater than the value 220-3.

According to one embodiment, based on the image obtained from the MRI-PET machine, PET image can be analyzed at block 204 to acquire data relating to the image, such data being used to obtain SUV parameter values for voxels that superimpose on the underlying tissue such that each voxel has a SUV parameter value 218 associated therewith. As done above, each SUV parameter value 218 can be compared with its respective threshold value 220-4 to determine whether the SUV parameter value 218 is greater than (or equal to) its corresponding threshold value 220-4.

According to yet another embodiment, at block 222, comparison outputs of all parameter values with their respective threshold values 220 for all voxel can be processed to determiner, for each voxel, parameters that have their respective values greater than corresponding threshold values 220. For instance, it can be determined at block 222 as to for voxel V1, how many of the four parameters have their values greater than (or equal to) corresponding threshold values 220. Based on the processing of the comparison outputs, at block 224, each voxel can be associated with a color indicative of the number of parameters that have their values greater than (or equal to) corresponding threshold values 220. For instance, a first color can be associated when all four parameters have their values greater than (or equal to) respective threshold values 220. A second color can be associated when three of the four parameters have their values greater than (or equal to) respective threshold values 220. A third color can be associated when two of the four parameters have their values greater than (or equal to) respective threshold values 220, and a fourth color can be associated when only one parameter has its value greater than (or equal to) respective threshold value 220.

At block 226, based on a color being associated with each voxel of the voxel grid, a colored voxel grid can be generated and presented to the user of the MRI-PET image, which colored voxel grid can then be used for analysis and classification/categorization/characterization of the tissue in context, as shown in block 228. For instance, in case the color is indicative of a situation when all the four parameters indicate the tissue part being malignant, a decision can be made by the user accordingly. As also mentioned above, any color combination can be configured for the implementation of the proposed disclosure. Even within four defined color, one or more shades can be configured based on parameter weights, voxels in context, tissue in context, designed/defined configuration, among other like attributes, number of threshold values for each of the four parameters.

Figure 3A:
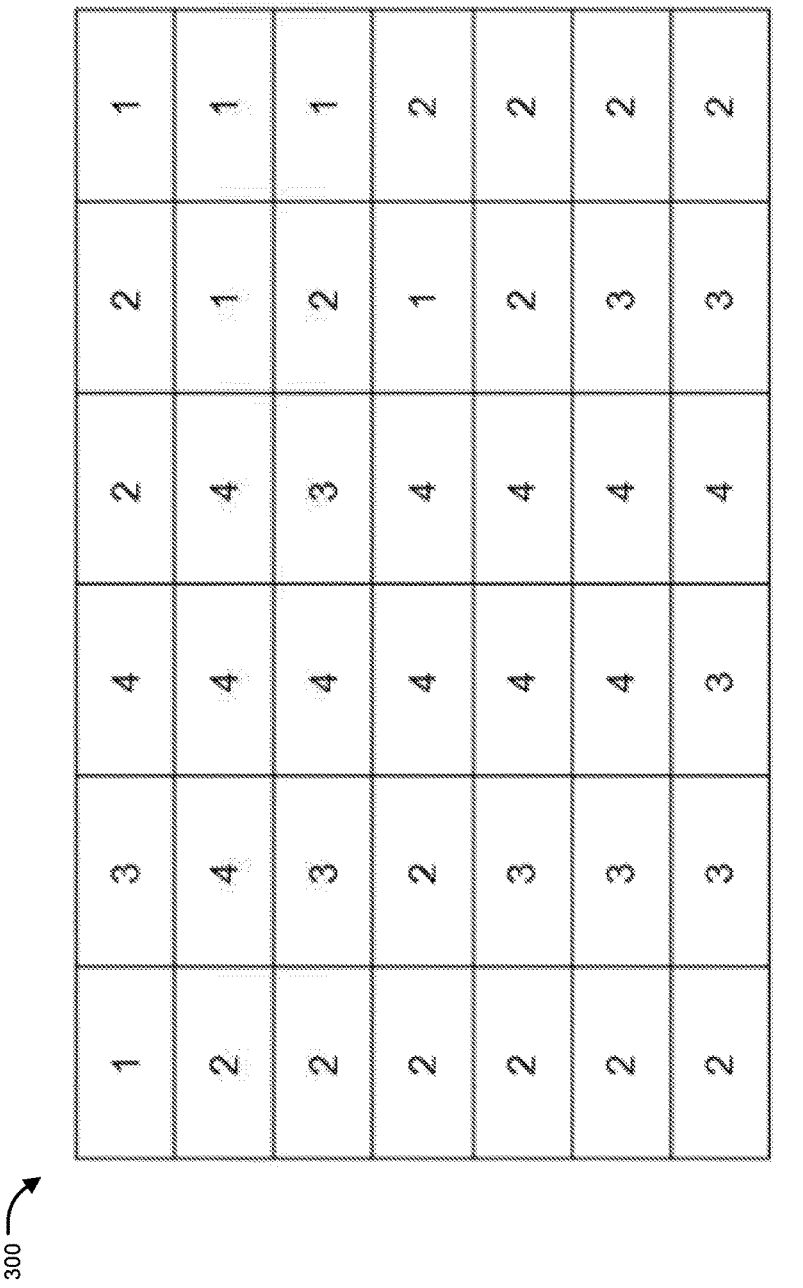
FIG. 3(*a*) illustrates an exemplary voxel grid showing colors (as codes) that are associated with each voxel of the grid to classify the tissue part underlying the grid.
Figure 3B:
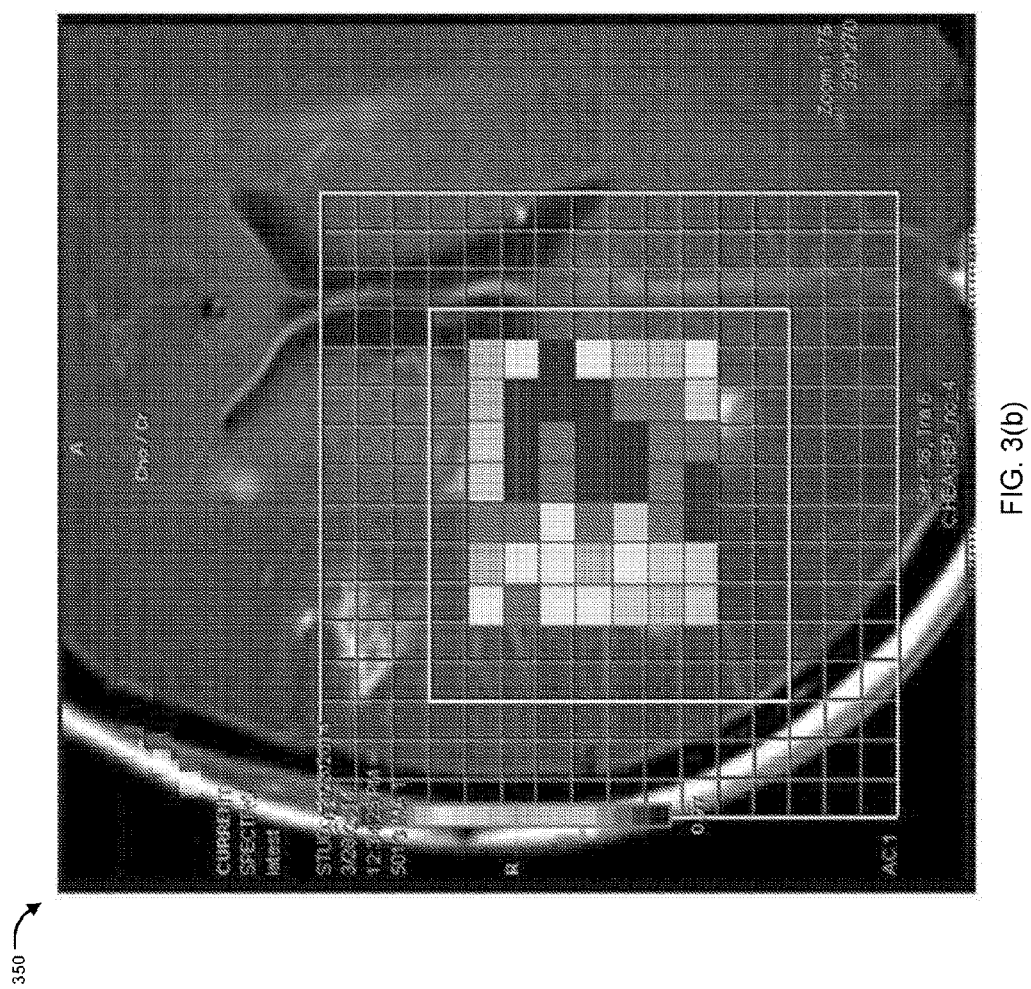

FIG. 3(*a*) illustrates an exemplary voxel grid 300 showing colors (as codes) that are associated with each voxel of the grid to classify the tissue part underlying the grid. According to one embodiment, for the purpose of the present example, grid can be considered as a 7 by 7 voxel grid, which can be superimposed over a tissue image obtained from MRI-PET machine. Table 1 illustrates parameter values obtained for ADC parameter for each voxel of the 7*7 grid. Table 2 illustrates parameter values obtained for CBV (normalized) parameter for each voxel of the 7*7 grid. Table 3 illustrates parameter values obtained for SUV (standard up take value) TBR (tumor to background ratio) parameter for each voxel of the 7*7 grid. Table 4 illustrates parameter values obtained for Cho/Cr parameter for each voxel of the 7*7 grid. For the purpose of the present disclosure, threshold value of CBV (normalized) parameter can be assumed to be 2.2, which can be assumed to be consistent for all the voxels of the grid. Similarly, threshold value of TBR (normalized) parameter for PET can be assumed to be 1.5, threshold value of Cho/Cr can be assumed to be 1.8, and threshold value of ADC can be assumed to be $1.00*10^{-3}$ mm²/sec.

TABLE 1

| | | | | | |
|---|---|---|---|---|---|
| 1.065 | 0.956 | 0.976 | 0.941 | 0.807 | 0.698 |
| 1.083 | 1.014 | 1.077 | 0.885 | 0.826 | 0.8 |

TABLE 1-continued

| | | | | | |
|---|---|---|---|---|---|
| 1.092 | 1.001 | 1.041 | 0.878 | 0.939 | 1.018 |
| 0.939 | 0.99 | 0.988 | 0.848 | 1.158 | 1.997 |
| 0.923 | 1.03 | 0.995 | 1.16 | 1.373 | 2.135 |
| 0.865 | 1.114 | 0.934 | 1.077 | 0.877 | 1.204 |
| 0.936 | 0.949 | 0.877 | 0.864 | 0.804 | 0.679 |

TABLE 2

| | | | | | |
|---|---|---|---|---|---|
| 1.6 | 3 | 4.6 | 4.1 | 1.1 | 0.7 |
| 3.5 | 4.3 | 5 | 4.3 | 1.4 | 1.4 |
| 1.8 | 2.9 | 4.4 | 4.9 | 4.4 | 2.5 |
| 2.8 | 3.5 | 4.3 | 5.2 | 3.2 | 5.1 |
| 1.3 | 1.9 | 5.4 | 4.8 | 2.4 | 1.6 |
| 1.2 | 2.3 | 5.4 | 4.3 | 1.6 | 2 |
| 1 | 2.3 | 3.1 | 4.7 | 2.3 | 2.2 |

TABLE 3

| | | | | | |
|---|---|---|---|---|---|
| 1.214759 | 1.73385 | 1.790214 | 1.304118 | 0.966417 | 0.862781 |
| 1.376043 | 2.059037 | 2.134759 | 1.592995 | 1.080802 | 0.840107 |
| 1.260374 | 1.981176 | 2.133636 | 1.69492 | 1.294706 | 0.88754 |
| 1.281016 | 2.052888 | 2.115561 | 1.802888 | 1.314813 | 0.821337 |
| 1.310481 | 2.072727 | 2.189626 | 1.739091 | 1.337112 | 0.878717 |
| 1.498289 | 2.185241 | 2.264492 | 1.966578 | 1.563957 | 1.140428 |
| 1.203636 | 1.750053 | 1.862353 | 1.999733 | 1.58016 | 1.059679 |

TABLE 4

| | | | | | |
|---|---|---|---|---|---|
| 1.4 | 1.7 | 2.2 | 15.0 | 14.8 | 1.1 |
| 2.0 | 1.8 | 3.0 | 2.2 | 1.2 | 1.2 |
| 2.0 | 1.8 | 1.8 | 1.0 | 1.2 | 1.1 |
| 2.2 | 1.0 | 2.0 | 2.5 | 1.1 | 1.2 |
| 2.6 | 3.4 | 2.7 | 3.0 | 1.6 | 1.6 |
| 2.5 | 5.4 | 3.5 | 1.7 | 2.5 | 1.9 |
| 1.6 | 2.6 | 3.9 | 2.3 | 1.9 | 1.8 |

Based on the above figures, value of each parameter can be compared with its respective threshold value for each voxel in order to indicate, for each voxel, the number of parameters that have their values greater than (or equal to) respective threshold values. For instance, for the first grid location in 1*1, only ADC parameter value 1.065 is greater than its respective threshold value, and all other three parameters CBV, SUV, and Cho/Cr have their values (1.6, 1.214759, 1.4) lower than respective thresholds (2.2, 1.5, 1.8), and therefore in FIG. 3(*a*), the 1*1 grid can be mapped to a defined color say Yellow, which for simplicity of the present disclosure can be referred to as 1. One should appreciate that instead of the color, even such codes (1-4) or any other defined/desired format can be used to present the voxel grid. In a similar example, for the third grid of the top row (from left to right), all the parameters have their values (0.976, 4.6, 1.790214, 2.2) greater than respective thresholds (0.001, 2.2, 1.5, 1.8), and therefore the voxel can be represented by a color, say Red, which has been coded as 4 in the instant FIG. 3(*a*). Similarly, in case three parameters have their values greater than respective thresholds, a brown color or any other defined representation can be used (represented as 3 in the instant disclosure), and in case two parameters have their values greater than respective thresholds, a green color or any other defined representation can be used (represented as 2 in the instant disclosure).

FIG. 3(*b*) illustrates a colored representation 350 of the voxel grid in accordance with an embodiment of the present disclosure. As seen, each voxel in the grid can be represented in a defined color, chosen from a set of four colors, depending on the number of parameters of that voxel that have their values greater than the respective thresholds.

Figure 4:
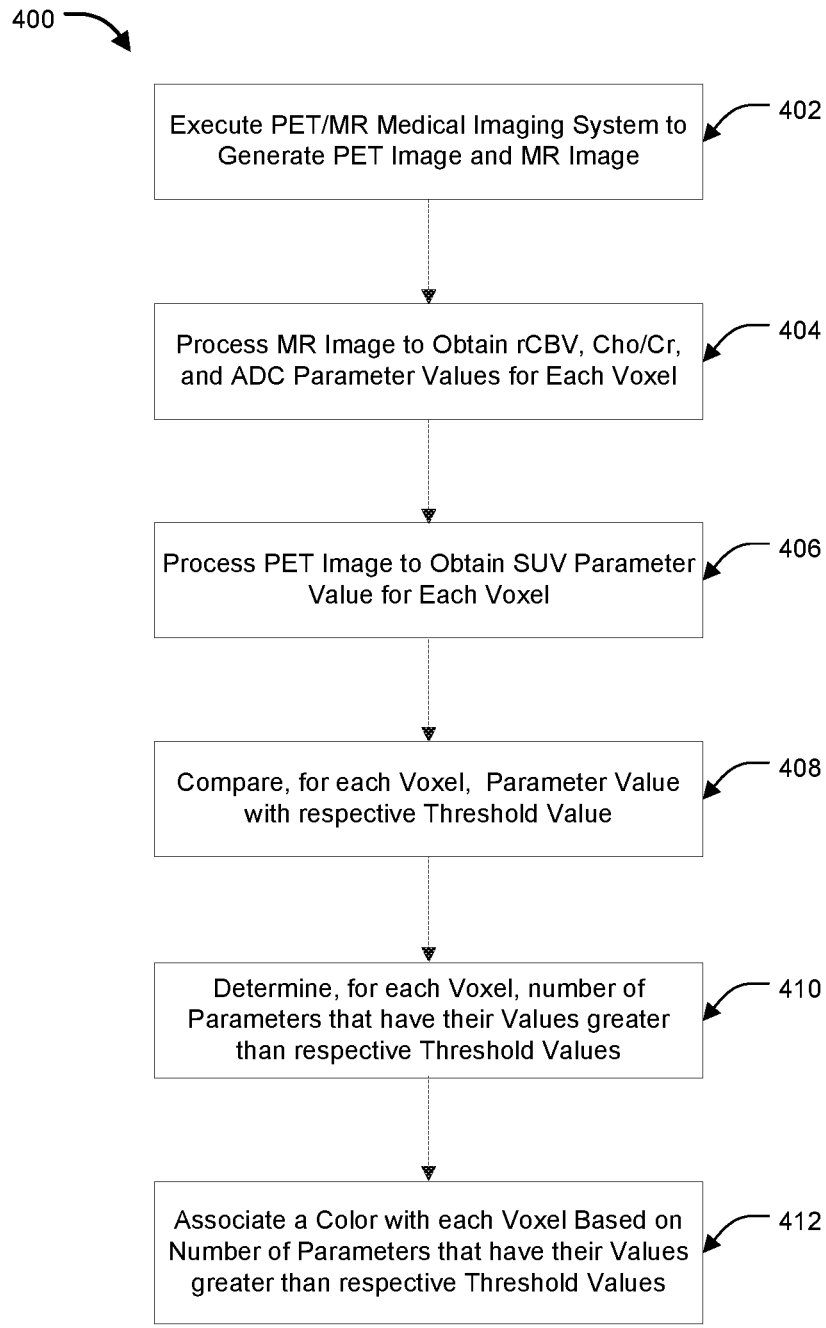
FIG. 4 illustrates an exemplary flow diagram for generating and analyzing a colored voxel grid to determine whether a tissue or part thereof is malignant in accordance with an embodiment of the present disclosure.

FIG. 4 illustrates an exemplary flow diagram 400 for generating and analyzing a colored voxel grid to determine whether a tissue or part thereof is malignant in accordance with an embodiment of the present disclosure. At step 402, a MRI-PET device can be used to generate and/or obtain a MRI image and a PET image. At step 404, the MRI image can be processed to obtain parameter values for each parameter rCBV, Cho/Cr, and ADC for each voxel of a voxel grid. At step 406, the PET image can be processed to obtain parameter values for SUV parameter for each voxel of a voxel grid. At step 408, each parameter value for each voxel can be compared with its respective threshold value to determine whether the concerned parameter value is greater than its respective threshold value. At step 410, for each voxel, number of parameters that have their values greater than their respective threshold value are determined. At step 412, based on the number of parameters that have their values greater than their respective threshold value, a color can be associated with each voxel to generate a colored voxel grid.

FIG. 5 illustrates an exemplary computer system diagram 500 used for generating and analyzing a colored voxel grid to determine whether a tissue or part thereof is malignant in accordance with an embodiment of the present disclosure. FIG. 5 illustrates a hardware layout of a system 500 for automated vessel segmentation, automated tissue segmentation or for computer aided tumor grading in accordance with various embodiments of the invention. The system 500 can include a has means 504 for receiving or accessing image data to be processed from an image recording apparatus such as a CT, MR, or PET scanner 502. Alternatively, 502 may represent an internal or external storage holding images recorded by such apparatus. The means 504 may e.g. be a data bus allowing access to a memory, an internet connection, or a cable or wireless connection. The system comprises a computer 506 or a similar processing apparatus holding an electronic processor 508 and memory 510 for holding and executing computer programs for vessel segmentation, tissue segmentation, histogram analysis and/or tumor grading using the received image data, such as BV maps containing BV values and other contrast images for identifying and selecting relevant tumor regions. After processing the received image data, the resulting vessel mask, segmented tumor region, or histogram/tumor grade could be applied in further (post)processing or displayed, printed etc. The system therefore also has means 512 for transmitting the result to a display 514, a printer, or to a further processing 516, e.g. a cable, data bus, Internet connection or similar.

In relation to FIG. 5, it is noted that the invention can be implemented by means of hardware, software, firmware or any combination of these. The invention or some of the features thereof can also be implemented as software running on several, potentially distributed, data processors and/or digital signal processors. The individual elements of an embodiment of the invention may be physically, functionally and logically implemented in any suitable way such as in a single unit, in a plurality of units or as part of separate functional units.

In another embodiment, system of the present disclosure can include a workstation that includes an input device (e.g., a keyboard, a mouse, a stylus, a touchscreen, a directional pad, a microphone, or any other suitable input device) via which a user enters information into the system. The workstation also includes a memory that stores, and a processor that executes, computer-executable instructions (e.g., routines, programs, algorithms, software code, etc.) for performing the various functions, methods, procedures, etc., described herein. The system further includes a display on which information is presented to the user. Additionally, "module," as used herein, denotes a set of computer-executable instructions, software code, program, routine, or other computer-executable means for performing the described function, or the like, as will be understood by those of skill in the art. Additionally, or alternatively, one or more of the functions described with regard to the modules herein may be performed manually.

According to one embodiment, it has been found therefore that a combination of rCBV, Cho/Cr, ADC, and SUV parameters for evaluation of their values and comparison of such values with respective parameter thresholds significantly enhances the accurate/reliable characterization of a tissue for malignancy detection, along with contributing to delineation of glioblastomas(within region of interest), offering information not available with conventional MRI. This approach may enhance the assessment of brain (tissue) gliomas, providing useful information for guiding stereotactic biopsies, easier detections, surgical resection and radiation treatment(or any other therapy).

In another aspect, although the present disclosure has been explained with respect with to one threshold value for each parameter, one should appreciate that multiple threshold values can be configured for each parameter such as ADC or SUV, wherein each such threshold value can help classify the underlying tissue part as being malignant, or normal or benign or help present/evaluate any other attribute of the tissue part. Classification of each tissue part based on a combination of the above-mentioned four parameters with respect to one or more parameter-threshold values can help characterize the tissue part more comprehensively and accurately with multiple attributes.

In another aspect, although the color coding for each voxel has been described with respect to four colors (depending on the number parameters that have their values above a defined threshold), any number of colors can be configured for a combination of the four parameters depending on the number of threshold values, mode of comparison, weight of each parameter, way in which the parameter values have been combined for visual presentation. Therefore, one should appreciate that all such color combinations, mode of combination of parameters, and association of color-coding to voxels of a grid are completely within the scope of the present disclosure.

One should appreciate that although most embodiments of the present disclosure have been described with respect to a MRI-PET device, the present invention can also be practice by separately taking MRI parameters from an MRI device and taking PET parameters from a PET device, and processing the parameter outputs for each voxel by comparing their values with respective thresholds.

According to another embodiment, as a single session study, we can have contrast dynamic (DCE) MRI only once. It is also possible to have $K_{trans}$ from DCE MRI, and rCBV derived from ASL (arterial spin labelling), which is a MRI technique done without injecting contrast. In this case we can have a fifth yet a strong tissue parameter into our analysis.

According to another embodiment, in case none of the parameters have their values above respective thresholds, either no color or a fifth new color can be associated with the voxel in order to make the analysis of the grid easier to make a decision on malignancy of the tissue or part thereof in context.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously. Within the context of this document terms "coupled to" and "coupled with" are also used euphemistically to mean "communicatively coupled with" over a network, where two or more devices are able to exchange data with each other over the network, possibly via one or more intermediary device.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

We claim:

1. A method for tissue classification comprising the steps of:
  acquiring MRI image of a tissue to be classified;
  acquiring PET image of said tissue;
  superimposing a voxel grid on said acquired MRI and/or PET images;
  determining, for each voxel of said grid, at least cerebral blood volume (rCBV) parameter value, and Choline/Creatine ratio (Cho/Cr) parameter value, and apparent diffusion coefficient (ADC) parameter value based on said MRI image;
  determining, for each said voxel of said grid, at least maximum standardized uptake value (SUV Max) parameter value based on said PET image;
  comparing, for each said voxel of said grid, rCBV parameter value, Cho/Cr parameter value, ADC parameter value, and SUV Max parameter value with respective threshold values to determine parameter values that are above respective threshold values;
  associating a color with each said voxel of said grid based on said comparison; and
  classifying said tissue based on color association to each voxel of said grid, wherein each of said rCBV parameter value, said Cho/Cr parameter value, said ADC parameter value, and said SUV Max parameter value has an importance weight; and color association to each said voxel of said tissue is based on a combination of parameter values being greater than respective threshold and the importance weight of each parameter value.

2. The method of claim 1, wherein a first color is associated with said voxel when each of said rCBV parameter value, said Cho/Cr parameter value, said ADC parameter value, and SUV Max parameter value is greater than respective threshold value.

3. The method of claim 1, wherein a second color is associated with said voxel when any three of said rCBV parameter value, said Cho/Cr parameter value, said ADC parameter value, and said SUV Max parameter value is greater than respective threshold value.

4. The method of claim 1, wherein a third color is associated with said voxel when any two of said rCBV parameter value, said Cho/Cr parameter value, said ADC parameter value, and said SUV Max parameter value is greater than respective threshold value.

5. The method of claim 1, wherein a fourth color is associated with said voxel when any one of said rCBV parameter value, said Cho/Cr parameter value, said ADC parameter value, and said SUV Max parameter value is greater than respective threshold value.

6. The method of claim 1, wherein classification of said tissue is done to evaluate whether said tissue or any part thereof is malignant.

7. The method of claim 1, wherein said MRI image and said PET image is obtained from a MR1-PET device.

8. The method of claim 1, wherein said MRI image and said PET image are obtained from a MRI system and PET device separately.

9. A system for tissue classification comprising:
  a MR-PET image generation module configured to acquire MRI image and PET of a tissue to be classified;
  a MR-PET image voxel grid overlay module configured to superimpose a voxel grid on said acquired MRI and/or PET images;
  a MR image based parameter quantification module configured to determine, for each voxel of said grid, at least cerebral blood volume (rCBV) parameter value, and Choline/Creatine ratio (Cho/Cr) parameter value, and apparent diffusion coefficient (ADC) parameter value based on said MRI image, wherein each of said rCBV parameter value, said Cho/Cr parameter value, and said ADC parameter value has an importance weight;
  a PET image based parameter quantification module configured to determine, for each said voxel of said grid, at least maximum standardized uptake value (SUV Max) parameter value based on said PET image, wherein said SUV Max parameter value has an importance weight;
  a parameter processing module configured to compare, for each said voxel of said grid, rCBV parameter value, Cho/Cr parameter value, ADC parameter value, and SUV Max parameter value with respective threshold values to determine parameter values that are above respective threshold values;
  a parameter processing based color association module configured to associate a color with each said voxel of said grid based on said comparison and the importance weight of each parameter value; and
  a colored-voxel grid presentation and analysis module configured to classify said tissue based on color association to each voxel of said grid.

* * * * *